United States Patent [19]

Liu et al.

[11] 4,263,427
[45] Apr. 21, 1981

[54] MONENSIN URETHANE DERIVATIVES

[75] Inventors: Chao-Min Liu; John Westley, both of Cedar Grove, N.J.

[73] Assignee: Hoffmann-La Roche Inc., Nutley, N.J.

[21] Appl. No.: 77,415

[22] Filed: Sep. 20, 1979

Related U.S. Application Data

[63] Continuation-in-part of Ser. No. 964,564, Nov. 29, 1978, abandoned.

[51] Int. Cl.$^3$ .............................................. C07H 3/08
[52] U.S. Cl. ........................................ 536/1; 424/180; 424/181; 435/72; 435/84; 536/17 R; 536/18; 536/53
[58] Field of Search ................ 536/17, 53, 18, 1, 17 R

[56] References Cited

U.S. PATENT DOCUMENTS

| | | | |
|---|---|---|---|
| 4,125,709 | 11/1978 | Smith | 536/53 |
| 4,138,481 | 2/1979 | Martin et al. | 536/17 |

OTHER PUBLICATIONS

Noller "Chem. of Organic Compounds", 3rd Ed., W. B. Saunders Co., Phila., Pa., 1965, pp. 338-339.
"Chemical Abstracts", vol. 70, 1969, pp. 2040g.

*Primary Examiner*—Johnnie R. Brown

*Attorney, Agent, or Firm*—Jon S. Saxe; Bernard S. Leon; Frank P. Hoffman

[57] ABSTRACT

Monensin urethane derivatives of the formula

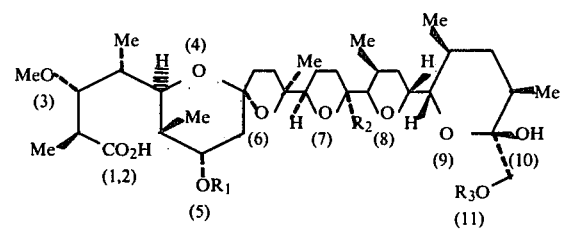

wherein $R_1$ is hydrogen, wherein $R_4$ is alkyl, aryl, alkylaryl, arylalkyl, haloaryl, nitroaryl, haloarylalkyl, alkoxyaryl, aryloxyaryl, arylcycloalkyl, acylaryl and cycloalkyl; $R_2$ is methyl or ethyl and $R_3$ is $-CONHR_4$ and their pharmaceutically acceptable salts.

The compounds exhibit antimicrobial activity and activity as growth promotant agents in ruminants. Further activities for this series of compounds are anticoccidial activity, antihypertensive activity, antimalarial activity and as agents in the treatment of swine dysentery.

Also disclosed are a fermentative process and a semisynthetic process for producing the urethane derivatives.

5 Claims, No Drawings

MONENSIN URETHANE DERIVATIVES

RELATED APPLICATIONS

This is a continuation-in-part application of copending U.S. Patent Application Ser. No. 964,564, filed Nov. 29, 1978 now abandoned.

BACKGROUND OF THE INVENTION

The present invention relates to monensin urethane derivatives of the formula

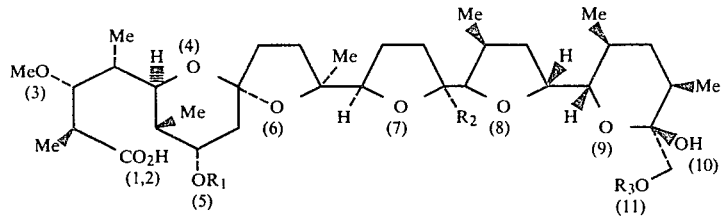

wherein $R_1$ is hydrogen, wherein $R_4$ is alkyl, aryl, alkylaryl, arylalkyl, haloaryl, nitroaryl, haloarylalkyl, alkoxyaryl, aryloxyaryl, arylcycloalkyl, acylaryl and cycloalkyl; $R_2$ is methyl or ethyl and $R_3$ is $—CONHR_4$ and their pharmaceutically acceptable salts.

The shorthand expression Me is utilized throughout to represent methyl.

The compounds of the present invention and their salts exhibit activity as antibacterial agents, growth promotant agents in ruminants, coccidiostats, antihypertensives, antimalarial agents and as agents in the treatment of swine dysentery.

By the term "acyl" is meant a $C_1$ to $C_7$, preferably a $C_1$ to $C_4$ alkanoic acid moiety, i.e., radicals of the formula

wherein R is $C_1$ to $C_6$ or hydrogen, e.g., acetyl, propionyl, butyryl and the like.

By the term "cycloalkyl" is meant cyclic hydrocarbon groups containing from 3 to 7 carbon atoms, such as, cyclopropyl, cyclobutyl, cyclohexyl and the like with cyclohexyl as preferred. The cycloalkyl group may be substituted by an aryl residue as defined herein to form an arylcycloalkyl residue, e.g., 2-(phenyl)-cyclopropyl.

By the term "alkoxy" is meant a $C_1$ to $C_7$ lower alkyl group having an oxygen function substituted therein, such as, methoxy, ethoxy, propoxy and the like.

The term "aryl" denotes an aromatic residue derived by the removal of a hydrogen atom from an aromatic hydrocarbon, such as, for example, phenyl, pyridyl or furyl, especially phenyl. Thereafter the "aryl" residue may be substituted by various groups. A substituent on a phenyl nucleous is preferably in 4-position such as in 4-alkylaryl, e.g., 4-methylphenyl(4-tolyl), 4-halophenyl, e.g., 4-chlorophenyl, 4-nitrophenyl, 4-aryloxy-aryl, e.g., 4-phenoxyphenyl, 4-alkoxyphenyl, e.g., 4-methoxyphenyl, 4-(alkyl-carbonyl)-phenyl, e.g., 4-(methylcarbonyl)phenyl or in 4-(phenylcarbonyl)phenyl.

By the term "alkyl" is meant a $C_1$ to $C_7$ straight or branched chain hydrocarbon, preferably a $C_1$ to $C_4$ hydrocarbon, e.g., methyl, ethyl, propyl, isopropyl, N-butyl, etc. The alkyl group may be substituted by an aryl residue as defined above to form an arylalkyl residue, e.g., phenylethyl or 2-phenylethyl or by a haloaryl residue to form a haloarylalkyl residue, e.g., 4-bromophenethyl.

Certain of the monensin urethane derivatives, viz. those of formula I wherein $R_4$ is phenethyl and their pharmaceutically acceptable salts, are produced by Streptomyces organisms designated as Strains X-14667, X-14573 and X-14575. Streptomyces sp. X-14667 was isolated from a soil sample collected from Aesculapius temple, Epidaurus, Greece. Streptomyces sp. X-14573 was isolated from a soil sample collected at the University of Arizona, Tempe, Ariz. Streptomyces sp. X-14575 was isolated from a soil sample collected in a corn field in the Catskills, N.Y., Streptomyces sp. X-14667, X-14573 and X-14575 were deposited with the United States Department of Agriculture, Agricultural Research Service, Northern Regional Research Laboratories (NRRL) Peoria, Ill. as lyophilized vials of the cultures. The cultures, given the identification numbers NRRL 11336 (X-14667), NRRL 11337 (X-14573) and NRRL 11338 (X-14575) (all deposited at NRRL on June 29, 1978) have been made available to the public through NRRL.

The cultures have also been deposited at the American Type Culture Collection, Rockville, Md. on August 23, 1979 and given the following accession numbers:

| | |
|---|---|
| X-14667 | ATCC 31551 |
| X-14573 | ATCC 31552 |
| X-14575 | ATCC 31553 |

The monensin urethane derivatives are polyether antibiotics and form a variety of pharmaceutically acceptable salts. These salts are prepared from the free acid form of the antibiotics by methods well-known for compounds of the polyether type in the art; for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts with the polyether compounds are lower alkyl amines, primary, secondary and tertiary hydroxy lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility which makes them amenable to parenteral use.

MORPHOLOGICAL CHARACTERISTICS

Representative strains of Streptomyces sp. X-14667, X-14573 and X-14575 have the following characteristics:

Sodium chloride tolerance, hydrolysis of casein and reduction of nitrate were determined by the methods recommended by Gordon and Smith, J. Bacteriol., 66, 41–48, 1953. Starch hydrolysis was determined after growth on agar of Actinomyces broth (Difco) with 0.25% soluble starch, and was tested by flooding the plates with iodine-KI solution. Gelatin hydrolysis was tested according to Skerman, (A Guide to Identification of the Genera of Bacteria, The Williams and Wilkins Co., Baltimore, 1967) using Actinomyces broth (Difco) with 2% agar in place of meat infusion agar. All tests were run at 28° C.

The standard ISP media of Shirling and Gottlieb were used for the description of growth and pigmentation (color determinations were made after two weeks of incubation at 28° C.). Carbon utilization was also determined by the method of Shirling and Gottlieb (Int. J. Syst. Bacteriol, 16, 313–340, 1966). A 24 hour old ISP-1 broth culture was homogenized and centrifuged to obtain a washed suspension for inoculation. The ability of the organism to grow at 10°, 28°, 37°, 45° and 50° C. was investigated by inoculating broth of ISP-1 (Difco) medium. Cell wall analysis was performed by the method of Becker et al. (Applied Microbiol. 12, 421–423, 1964).

Microscopic examination.

Strains X-14667, X-14573 and X-14575 produce a substrate mycelium which does not fragment into spores, and an aerial mycelium, which later forms spore chains. After 14 days of incubation at 28° C., the spore chains appear rectus-flexibilis in form with greater than 50 spores per chain. Spores are smooth and range in size from 0.70 by 0.5 $\mu$m to 1.35 by 0.38 $\mu$m for X-14667; 0.7 by 0.4 to 1.45 by 0.4 $\mu$m for X-14573; 0.8 by 0.5 $\mu$m to 0.6 by 1.0 $\mu$m for X-14575.

The cell wall of the cultures contains the LL isomer of diaminopimelic acid, which, together with the above characteristics places this organism in the genus Streptomyces (Lechevalier et al., Adv. Appl. Microbial., 14, 47–72, 1971).

Macroscopic examination.

In Tables 1, 2 and 3 are summarized the amount of growth, degree of sporulation, spore mass color, color of reverse substrate mycelium, and presence of a soluble pigment produced by strain X-14667, X-14573 and X-14575 on various solid media.

TABLE 1

| Agar Medium | Amount of Growth Degree of Sporulation | Spore Mass Color[a] | Color of Reverse Substrate Mycellium[a] |
|---|---|---|---|
| Yeast malt extract (SIP-2)[b] | moderate growth; moderate sporulation | b (oyster white) | 3lg (adobe brown) |
| Oatmeal (ISP-3)[b] | moderate growth; moderate sporulation; slightly pink reverse which turned blue with NaOH | b (oyster white) | 5ge (rose wood) |
| Inorganic salts starch (ISP-4)[b] | abundant growth; abundant sporulation; hydrolysis starch | 3cb (sand) | 5ie (copper tan) |
| Glycerol asparagine (ISP-5)[b] | moderate growth; abundant sporulation | b (oyster white) | 3lg (adobe brown); edge of 2cc (biscuit) |
| Czapek-Dox[c] | abundant growth; abundant sporulation | 3dc (natural) | 2gc (bamboo); edge of 2ec (biscuit) |

[a]The color scheme used was that taken from the Color Harmony Manual, 4the ed., 1958 (Container Corporation of America, Chicago).
[b]Media recommended by the International Streptomyces Project. (Shirling, E.B. & D. Gottieb, Int. J. Syst. Bacteriol. 16, 313–340, 1966).
[c]Czapek-Dox broth (BBL) to which 1.5% agar was added.

TABLE 2

| Agar Medium | Amount of Growth; Degree of Sporulation | Spore Mass Color[a] | Color of Reverse Substrate Mycelium[a] |
|---|---|---|---|
| Yeast malt extract (ISP-2)[b] | abundant growth; well sporulated; dark red-brown soluble pigment | 3cb (sand) | 5nl (chocolate) |
| Oatmeal (ISP-3)[b] | moderate to abundant growth; moderate sporulation | b (oyster white) | 4ie (cork tan) |
| Inorganic salts-starch (ISP-4)[b] | abundant growth; well sporulated; hydrolyzes starch; brown soluble pigment | 5cb (no name) | 4nl (chocolate) |
| Glycerol-asparagine (ISP-5)[b] | abundant growth; well sporulated; brown soluble pigment; hygroscopic | 3dc (natural) | 4nl (chocolate) |
| Czapek-Dox[c] | moderate to abundant | 3cb (sand) | 4ie (cork tan) |

TABLE 2-continued

CULTURAL CHARACTERISTICS OF STRAIN X-14573

| Agar Medium | Amount of Growth; Degree of Sporulation | Spore Mass Color[a] | Color of Reverse Substrate Mycelium[a] |
|---|---|---|---|
| | growth; well sporulated | | |

[a] The color scheme used was that taken from the Color Harmony Manual, 4th ed., 1958 (Container Corporation of America, Chicago).
[b] Media recommended by the International Streptomyces Project. (Shirling, E.B. & D. Gottieb, Int. J. Syst. Bacteriol. 16, 313-340, 1966).
[c] Czapek-Dox broth (BBL) to which 1.5% agar was added.

TABLE 3

CULTURAL CHARACTERISTICS OF STRAIN X-14575

| Agar Medium | Amount of Growth; Degree of Sporulation | Spore Mass Color[a] | Color of Reverse Substrate Mycelium[a] |
|---|---|---|---|
| Yeast malt extract (ISP-2)[b] | moderate growth; sparse sporulation; brown soluble pigment | b (oyster white) | 4nl (chocolate) |
| Oatmeal (ISP-3)[b] | moderate growth; moderate sporulation | b (oyster white) | 3ec (bisque) mostly; 3lg (adobe brown) in spots |
| Inorganic salts-starch (ISP-4)[b] | moderate growth; moderate sporulation; hydrolyzes starch; brownish soluble pigment where not hydrolyzed | b (oyster white) | 3lg (adobe brown) |
| Glycerol-asparagine (ISP-5)[b] | moderate growth; no sporulation | 3lg (adobe brown) 3ie (camel) at isolated edges; not sporulated | 3ie (camel) |
| Czapek-Dox[c] | moderate growth; sparse sporulation | 4lg (light spice brown) mostly where non-sporulated, b (oyster white) where sporulated in patches | 4ie (cork tan) |

[a] The color scheme used was that taken from the Color Harmony Manual, 4th ed., 1958 (Container Corporation of America, Chicago).
[b] Media recommended by the International Streptomyces Project. (Shirling, E.B. & D. Gottieb, Int. J. Syst. Bacteriol. 16, 313-340, 1966).
[c] Czapek-Dox broth (BBL) to which 1.5% agar was added.

Physiological characteristics.

Tables 4 and 5 report the results of carbon utilization and metabolic characteristics of strains X-14667, X-14573 and X-14575 and compares the results with those of the patented strain, S. cinnamonensis, 1712A which produces monensin.

TABLE 4

Comparison of carbon utilization of Strains X-14667, X-14573, X-14575 and S. cinnamonensis

| Carbon Source | Growth response* of: | | | S. cinnamonensis 1712A |
|---|---|---|---|---|
| | X-14667 | X-14573 | X-14575 | |
| D-Glucose | ++ | ++ | ++ | ++ |
| D-Xylose | + | ++ | ++ | ++ |
| L-Arabinose | ++ | ++ | ++ | +(+) |
| L-Rhamnose | − | ++ | − | ++ |
| D-Fructose | +(+) | ++ | ++ | ++ |
| D-Galactose | ++ | ++ | ++ | ++ |
| Raffinose | ++ | +(+) | ++ | +(+) |
| D-Mannitol | ++ | ++ | ++ | ++ |
| i-Inositol | + | ++ | ++ | ++ |
| Salicin | ± to + | ++ | ++ | +(+) |
| Sucrose | − | − | − | − |
| Cellulose | − | − | − | − |

*−, Negative response; ±, doubtful response; +, more growth than on carbon control but less than on glucose; ++, positive response equal to the amount of growth on glucose.

TABLE 5

METABOLIC CHARACTERISTICS

| Test | X-14667 | X-14573 | X-14575 | S. cinnamonensis 1712A |
|---|---|---|---|---|
| ISP-6 darkening | − | − | − | − |
| Melanin, ISP-7 | − | − | − | − |
| Casein hydrolysis | + | + | + | + |
| Gelatin hdrolysis | + | + | + | + |
| Starch hydrolysis | + | + | + | + |
| NaCl (%) tolerance | <10, probably = 7% | 7 | 7 | <10 |
| Growth range temp (°C.) | 10-37 | N.D. | N.D. | 10-37 |
| ISP-1 darkening | − | +, redwood | ± slightly brownish | + slight |
| Reverse-side pigment | slightly red-brown | brown | brown, occasionally | brownish occasionally |
| Soluble pigment | pink; reversible | red-brown | brown | brownish |

TABLE 5-continued

METABOLIC CHARACTERISTICS

| Test | X-14667 | X-14573 | X-14575 | S. cinnamonensis 1712A |
|---|---|---|---|---|
| Antibiotic | to blue with NaOH * | * | * | |
| production | ** | ** | ** | monensin |
| Nitrate reduction | + | ± | + | ± in 2 wks |
| Hyroscopic property | + | slight on ISP-5 | − | − |

N.D. = not determined
*Monensin A, 2-phenethylurethane
**Monensin B, 2-phenethylurethane A comparison of the description of strains X-14667, X-14573 and X-14575 with those of the Streptomyces species described in Bergey's Manual (Buchanan and Gibbons, ed., Bergey's Manual of Determination Bacteriology, 8th ed., 748–829, 1974), H. Nonomura's key for classification (J. Ferment. Technol., 52, 78–92, 1974) and Pridham and Lyons' classification (Dev. Ind. Microbiol. 10, 183–221, 1969), showed that *S. cinnamonensis* is the closest relative to the above strains based on the following combination of criteria: gray spore mass color, rectus-flexibilis spore chain form, smooth spore surface, chromogenic reaction on ISP media 1 and 6, and carbon utilization characteristics. *S. cinnamonensis,* is similar to X-14667, X-14573 and X-14575 in that they all produce monensin A and monensin B. However, *S. cinnamonensis,* differs from the above strains since it does not produce any of the monensin phenethylurethanes.

The Streptomyces species X-14667, X-14573 and X-14575 described herein include all strains of Streptomyces which form compounds as disclosed in the present application and which cannot be definitely differentiated from the strains NRRL 11336, 11337 and 11338 and their subcultures including mutants and variants. The claimed compounds are described herein and after this identification is known, it is easy to differentiate the strains producing these compounds from others.

Streptomyces X-14667, X-14573 and X-14575 when grown under suitable conditions, produces monensin urethane derivatives. A fermentation broth containing Streptomyces X-14667, X-14573 or X-14575 is prepared by inoculating spores or mycelia of the organism producing the derivatives into a suitable medium and then cultivating under aerobic conditions. For the production of the derivatives, cultivation on a solid medium is possible but for producing in large quantities, cultivation in a liquid medium is preferable. The temperature of cultivation may be varied over a wide range, 20°–35° C., within which the organism may grow but a temperature of 26°–30° C. and a substantially neutral pH are preferred. In the submerged aerobic fermentation of the organism for the production of the monensin derivatives, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, as anti-foam agent such as liquid paraffin, fatty oils or silicone compounds is used. More than one kind of carbon source, nitrogen source or anti-foam source may be used for production of the monensin derivatives.

The antibiotic activity of the monensin urethane derivatives is illustrated by the following table (Table 6):

TABLE 6

Antimicrobial Species of Urethane Derivatives of Monensins
Minimum Inhibitory Concentration (meg/ml)[a]

| | Staph. aureus 6538 | Sarcina lutca 9341 | Streptococcus faecium 8043 | Bacillus sp. E 27859 | Bacillus subtilis 583[b] | Bacillus megaterium 8CU | Bacillus sp. TA 27860 | Myco-Bacterium phlei 355 | Streptococcus cellulosac 3313 | Paceilomyces variotl 25820 |
|---|---|---|---|---|---|---|---|---|---|---|
| Monensin B,2-phenethylurethane (natural product) | 6.3 | 3.1 | 0.8 | 1.6 | 3.1 | 3.1 | 3.1 | 25 | 12.5 | — |
| Monensin A,2-phenethylurethane (natural product) | 6.3 | 1.6 | 0.4 | 0.8 | 1.6 | 0.8 | 1.6 | 6.3 | 12.5 | 12.5 |
| Monensin B,(R)-1-phenethyl-urethane | 6.3 | 3.1 | 0.8 | 0.4 | 1.6 | 1.6 | 1.6 | 12.5 | 3.1 | 3.1 |
| Monensin B,(S)-1-phenethyl-urethane | 1.6 | 1.6 | 0.2 | 0.1 | 0.8 | 0.4 | 0.2 | 6.3 | 6.3 | 6.3 |
| Monensin A,4-bromophenyl urethane | 0.8 | 0.2 | 0.1 | 0.05 | 0.4 | 0.1 | 0.2 | 1.6 | 0.8 | 1.6 |
| Monensin A,4-chlorophenyl urethane | 0.4 | 0.2 | 0.05 | 0.02 | 0.4 | 0.2 | 0.2 | 0.8 | 0.8 | 3.1 |
| Monensin A,phenylurethane | 0.8 | 0.8 | 0.1 | 0.05 | 0.4 | 0.4 | 0.4 | 3.1 | 3.1 | 3.1 |
| Monensin A,4-flurophenyl urethane | 1.6 | 0.8 | 0.1 | 0.2 | 0.8 | 0.4 | 0.8 | 3.1 | 3.1 | 3.1 |
| Monensin A,cyclohexyl-urethane | 1.6 | 0.8 | 0.1 | 0.2 | 0.8 | 0.4 | 0.6 | 3.1 | 3.1 | 3.1 |
| Monensin A,2-(phenyl)-cyclo- | 3.1 | 0.8 | 0.2 | 0.4 | 0.8 | 0.8 | 0.4 | 3.1 | 12.5 | 6.3 |

TABLE 6-continued
Antimicrobial Species of Urethane Derivatives of Monensins
Minimum Inhibitory Concentration (meg/ml)[a]

|  | Staph. aureus 6538 | Sarcina lutca 9341 | Streptococcus faecium 8043 | Bacillus sp. E 27859 | Bacillus subtilis 583[b] | Bacillus megaterium 8CU | Bacillus sp. TA 27860 | MycoBacterium phlei 355 | Streptococcus cellulosac 3313 | Paceilomyces variotl 25820 |
|---|---|---|---|---|---|---|---|---|---|---|
| propyl urethane |  |  |  |  |  |  |  |  |  |  |
| Monensin A,methylurethane | 25 | 25 | 1.6 | 6.3 | 1.6 | 6.3 | 12.5 | — | — | — |
| Monensin A,n-butylurethane | 1.6 | 1.6 | 0.2 | 0.2 | 0.4 | 0.8 | 0.4 | 6.3 | 3.1 | 6.3 |
| Monensin A,4-(methylcarbonyl) phenylurethane | 1.6 | 1.6 | 0.8 | 0.2 | 1.6 | 1.6 | 0.8 | 6.3 | 3.1 | 6.3 |
| Monensin A,4-phenoxyphenylurethane | 0.4 | 0.4 | 0.1 | 0.4 | 0.4 | 0.4 | 0.2 | 1.6 | 0.8 | 0.8 |
| Monensin A,4-methoxyphenylurethane | 1.6 | 1.6 | 0.4 | 0.1 | 0.8 | 0.8 | 6.3 | 1.6 | 6.3 |  |
| Monensin A,4-methylphenylurethane | 0.4 | 0.4 | 0.2 | 0.05 | 0.4 | 0.2 | 0.2 | 1.6 | 0.8 | 1.6 |

(a) Lowest two-fold dilution giving zone of inhibition in the agar-well diffusion assay.
(b) NRRL collection number, all the rest ate ATCC numbers.

From the above table (Table 6) which indicates the in vitro activity of the compounds of the present invention against certain gram-positive bacteria there is found the utility as an antibacterial agent useful in wash solutions for sanitary purposes as in the washing of hands and the cleaning of equipment, floors or furnishings of contaminated rooms or laboratories.

Further, it has been found that certain of the monensin urethane derivatives presently disclosed, viz. those of formula I wherein $R_4$ is aryl, haloaryl, nitroaryl, alkylaryl or cycloalkyl and their pharmaceutically acceptible salts exhibit anti-coccidal activity versus the organism *Eimeria tenella*.

This anti-coccidal activity is demonstrated on laboratory chickens as follows:
Test method This test utilizes ten chickens per drug group. Ten chickens are employed as a weight control and ten chickens as an infected control. The drug is given 48 hours in advance of the infection. One gm. of the test drug is mixed in a mechanical mixer with a sufficient amount of chicken feed to result in the desired dosage. The infection consists of approximately 200,000 oocysts given orally by pipette. The tests lasts for eleven days and then the surviving birds are autopsied and examined for gross lesions in the ceca. The test birds are rated according to the number of survivors and the number of cecal lesions. The results are expressed as average degree of infection (A.D.I.). An average degree of infection of less than 2.5 is considered to be significant.

TABLE 7
Anti-coccidial effects of monensin urethanes added to the feed of chickens infected with *Eimeria tenella*.

| Compound | Dosage in feed, ppm | Average Degree of Infected (A.D.I.) |
|---|---|---|
| Uninfected untreated control | none | 0.0 |
| Infected untreated control | none | 3.0 |
| Monensin A, 4-nitrophenylurethane | 75 | 0.5 |
| Monensin A, 4-bromophenylurethane | 75 | 0.7 |
| Monensin A, phenylurethane | 75 | 0.9 |
| Monensin A, 4-chlorophenylurethane | 65 | 0.8 |
| Monensin A, 4-methylphenylurethane | 75 | 1.1 |
| Monensin A, 4-iodophenylurethane | 125 | 0.1 |
| Monensin A, 4-fluorophenylurethane | 125 | 1.0 |
| Monensin A, cyclohexylurethane | 125 | 0.8 |

The monensin urethane derivatives have also been found to be active against *Treponema hyodysenteriae*.

The minimal inhibitory concentrations of the urethane derivatives are as follows:

| Compound | MIC(meg/ml) |
|---|---|
| Monensin B, 2-phenethylurethane (natural product) | 0.4-2.0 |
| Monensin B, 2-phenethylurethane (synthetic product) | 2.0 |
| Monensin A, 4-bromophenylurethane | 0.4 |
| Monensin B, (R)-1-phenethylurethane | 0.4 |
| Monensin A, 2-phenylurethane | 0.4 |
| Monensin A, phenylurethane | 0.08-0.4 |
| Monensin A, 4-chlorophenylurethane | 0.08 |
| Monensin B, (S)-1-phenethylurethane | 0.4 |
| Monensin A, cyclohexylurethane | 0.4 |
| Monensin A, 2-(phenyl)-cyclopropyl urethane | 0.4 |
| Monensin A, 4-florophenylurethane | 0.08 |

Testing for activity against *Treponema hyodysenteriae*, a cause of swine dysentery consisted of inoculation of blood agar plates containing a series of two or fourfold dilutions of the monensin urethane derivatives with tenfold dilutions of the *T. hyodysenteriae* strain. After 48 hours of incubation at 42° C. in an anerobic atmosphere, Minimum Inhibitory Concentrations were recorded as the lowest concentrations of compound which completely inhibited the most dilute inoculum of each *T. hyodysenteriae* strain.

The monensin urethane derivatives have further been found to exhibit activity as growth promotants in ruminants.

Administration of the monensin urethane derivatives hereafter "Antibiotics" or "Antibiotic Compounds" prevents and treats ketosis as well as improves feed utilization in ruminants or swine. The causative mechanism of ketosis is a deficient production of propionate compounds. A presently recommended treatment is administration of propionic acid or feeds which preferentially produce propionates. It is obvious that encouraging propionate production from ordinary feeds will reduce incidence of ketosis.

It has been found that the urethane derivatives increases the efficiency of feed utilization in ruminant animals when it is administered orally to the animals. The easiest way to administer the antibiotic is by mixing it in the animal's feed.

However, the antibiotic can be usefully administered in other ways. For example, they can be incorporated into tablets, drenches, boluses, or capsules, and dosed to the animals. Formulation of the antibiotic compounds in such dosage forms can be accomplished by means of methods well known in the veterinary pharmaceutical art.

Capsules are readily produced by filling gelatin capsules with any desired form of the desired antibiotic. If desired, the antibiotics can be diluted with an inert powdered diluent, such as a sugar, starch, or purified crystalline cellulose in order to increase their volume for convenience in filling capsules.

Tablets of the antibiotics are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose while magnesium carbonate is also useful for oily substance. Frequently used binders are gelatin, gums, starch, dextrin and various cellulose derivatives. Among the commonly used lubricants are magnesium stearate, talc, paraffin wax, various metallic soaps, and polyethylene glycol.

The administration of the antibiotic compounds may be as a slow-pay-out bolus. Such boluses are made as tablets except that a means to delay the dissolution of the antibiotics is provided. Boluses are made to release for lengthy periods. The slow dissolution is assisted by choosing a highly water-insoluble form of the antibiotics. A substance such as iron filing is added to raise the density of the bolus and keep it static on the bottom of the rumen.

Dissolution of the antibiotics is delayed by use of a matrix of insoluble materials in which the drug is imbedded. For example, substances such as vegetable waxes, purified mineral waxes, and water-insoluble polymeric materials are useful.

Drenches of the antibiotics are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotics can be prepared in nonsolvents such as vegetable oils such as peanut, corn, or sesame oil, in a glycol such as propylene glycol or a polyether glycol; or in water, depending on the form of the antibiotics chosen.

Suitable physiologically acceptable adjuvants are necessary in order to keep the antibiotics suspended. The adjuvants can be chosen from among the thickeners, such as carboxymethylcellulose, polyvinylpyrrolidone, gelatin, and the alginates. Many classes of surfactants serve to suspend the antibiotics. For example, lecithin, alkylphenol polyethylene oxide adducts, naphthalenesulfonates, alkylbenzesulfonates, and the polyoxyethylene sorbitan esters are useful for making suspensions in liquid nonsolvents.

In addition many substances which affect the hydrophilicity, density, and surface tension of the liquid can assist in making suspensions in individual cases. For example, silicone anti-foams, glycols, sorbitol, and sugars can be useful suspending agents.

The suspendable antibiotics may be offered to the grower as a suspension, or as a dry mixture of the antibiotics and adjuvants to be diluted before use.

The antibiotics may also be administered in the drinking water of the ruminants. Incorporation into drinking water is performed by adding a water-soluble or water-suspendable form of the antibiotics to the water in the proper amount. Formulation of the antibiotics for addition to drinking water follows the same principles as formulation of drenches.

The most practical way to treat animals with the antibiotic compounds is by the formulation of the compounds into the feed supply. Any type of feed may be medicated with the antibiotic compounds, including common dry feeds, liquid feeds, and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotics for useful treatment is well understood. It is necessary only to calculate the amount of compounds which it is desired to administer to each animal, to take into account the amount of feed per day which the animal eats and the concentration of antibiotic compounds in the premix to be used, and calculate the proper concentration of antibiotic compounds, or of premix, in the feed.

All of the methods of formulating, mixing and pelleting feeds which are normally used in the ruminant feed art are entirely appropriate for manufacturing feeds containing the antibiotic compounds.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum since it would be expected that a beneficial change in the propionate/acetate ration would occur upon oral administration of the instant antibiotics. Horses, swine and rabbits are exemplary animals which digest a part of their food by cecal fermentation.

DETERMINATION OF VOLATILE FATTY ACID (VFA) PRODUCTION

A bovine, surgically modified with a rumen fistula, is used as a source of rumen fluid. The integrity of the rumen is maintained by a rumen cannula (Bar Diamond Labs, Parma, Idaho) which is opened in order to obtain rumen fluid samples. The animal is fed twice daily an 30% concentrate (AHRES ration #39):20% roughage ration. The rumen fluid is obtained prior to the A.M. feeding. The rumen fluid is strained through 4 layers of cheesecloth into a 1 gallon Nalgene container and is kept under anaerobe quality $CO_2$. One thousand mls of the strained rumen fluid are added to 2000 mls of an ice cold buffer based upon that specified by Cheng et al., J. Dair. Sci., 38, 1225 (1955). The composition of this buffer is as follows:

| | | | |
|---|---|---|---|
| $Na_2HPO_4$ | 0.316 g/l | $MgSO_4$ | 0.112 |
| $KH_2PO_4$ | 0.152 | $CaCl_2$ | 0.038 |

| | | | |
|---|---|---|---|
| NaHCO$_3$ | 2.260 | FeSO$_4$ . 7H$_2$O | 0.008 |
| NaCl | 0.375 | ZnSO$_4$ . 7H$_2$O | 0.004 |
| KCl | 0.375 | CuSO$_4$ . 5H$_2$O | 0.002 |

The buffered rumen fluid is held in a 4 liter separatory funnel. In order to help maintain the anaerobic character of the rumen fluid and the homogeneity of the buffered rumen fluid, anaerobe quality CO$_2$ is bubbled constantly through the fluid in a separatory funnel beginning approximately ½" above the separatory funnel stopcock.

Two hundred and fifty ml Erlenmeyer flasks are used for individual fermentations. Each flask to which a compound will be added contains one gram of a finely ground 80% concentrate:20% alfalfa hay ration. Flasks which are to be used as drug-free controls contain 1.07 grams of the finely ground ration. One ml of test compound dissolved in an appropriate solvent is added to each flask and allowed to sit for ½ to 1 hour. Each compound is examined in duplicate flasks at a final concentration of 50 ppm. Solvent without test compound is added to drug-free control fermentation flasks. Monensin at 10 and 50 ppm is used as a positive control in all fermentations.

Eighty grams of buffered rumen fluid are added to each flask containing test compound and 85.93 grams are added to control flasks. Flasks to which all components have been added are stoppered with a gas collection apparatus and left sitting at room temperature until all flasks have been completed. Six ml samples are withdrawn from all control flasks as the 0 time samples. The incubation period and the collection of gas evolved during fermentation is initiated 10 minutes after the flasks have been placed in a 38° C. water bath. Flasks are incubated with shaking (90 oscillations per minute) for 4 hours.

The volume of gas produced by each fermentation is measured at ½ hour intervals. The manometric apparatus for collection of gas and measurement of the volume evolved has been described by Trei et al., J. Anim. Sci., 30, 825 (1970).

Rumen fluid is poured into 25×150 mm glass tubes and left in an ice bath for approximately 15 minutes to permit settling of particulate matter. The 6 ml quantity of rumen fluid is then added to a 2 ml quantity of 25% (W/V) metaphosphoric acid (J T Baker) in 13 ml polycarbonate centrifuge tubes (Autoclear, IEC). Each tube is stoppered and thoroughly mixed. Tubes are left in an ice bath for 30 minutes and then centrifuged at 16,000 rpms for 10 minutes in an 874 angle head in an IEC B20 centrifuge. A 1 ml quantity of the internal standard (0.25% 2-methyl valeric acid, Aldrich Chemical Company) is then added to a 4 ml quantity of the supernate. The resulting mixture is filtered through a 0.22 micron Millipore filter using a Swinnex filter and a 5 ml syringe. The filtrate is sealed in one ml glass vials with Teflon lined rubber crimp septa.

Each vial, representing each of the individual fermentations, is analyzed for volatile fatty acids.

Each vial is analyzed with three consecutive injections. Concentrations of acetate, propionate, i-butyrate, n-butyrate, i-valerate and n-valerate are calculated by comparison with analyses of a standard solution of VFA's using an internal standardization method.

The results are stated in the following table:

TABLE 8

Effect of miscellaneous ionophores on gas and VFA production in in vitro fermentations:

| Compound | Compound Concentration (ppm) | Percent Production of Control Fermentations | | |
|---|---|---|---|---|
| | | Total VFA | Rate of Gas Production | *Relative levels of propionate (C$_3$) to acetate + butyrate(C$_2$ + C$_4$) |
| Monensin B, 2-phenethyl urethane(natural product) | 10 | 157.8 | 93 | 129 |
| | 50 | 149.1 | 92 | 146 |
| Monensin | 10 | 110.7 | 85 | 162 |
| | 50 | 105.3 | 89 | 165 |
| Narasin | 10 | 102.5 | 88 | 166 |
| | 50 | 106.0 | 86 | 167 |
| Monensin A, 2-phenethylurethane(natural product) | 50 | 84.3 | 101.7 | 187 |
| Mono-(4-bromophenyl-urethane) of monensin | 50 | 89.9 | 103.0 | 165 |
| Monensin B, 1(R)-phenethylurethane | 50 | 82.7 | 103.3 | 167 |
| Control | 0 | 100 | 100 | 100 |

*The ratio of C$_3$:(C$_2$ + C$_4$) is normalized to a value of 100 for the untreated control.

Compounds of formula I wherein R$_4$ is aryl, haloaryl or nitroaryl and their pharmaceutically acceptable salts are orally active as antimalarial agents. This activity is demonstrated by the following activities against the malaria causing agent *Plasmodium berghei* in mice:

| Compound | ED$_{50}$mg/kg p.o. |
|---|---|
| Monensin A, 4-chlorophenylurethane | 2.3 |
| Monensin A, phenylurethane | 4 |
| Monensin A, 4-bromophenylurethane | 15-20 |

Compounds of formula I, and their pharmaceutically acceptable salts are orally active as antihypertensive agents. This activity is demonstrated by the following table (Table 9):

TABLE 9
NATURAL AND SEMI-SYNTHETIC MONENSIN URETHANES

| Compound | Oral Dose (mg/kg) | Day of Maximum Change (%) | | | | Mean Blood Pressure (mm Hg) | |
|---|---|---|---|---|---|---|---|
| | | Blood Pressure | | Heart Rate | | Before | At time of |
| | | days | change | days | change | treatment | maximum effect |
| Monensin B, 2-phenyl-1-ethyl urethane[b] | 10 | 2 | 13 | 3 | 14 | 216 | 189 |
| Monensin A, 2-phenyl-1-ethyl urethane[b] | 10 | 5 | 15 | 2 | 18 | 223 | 189 |
| Monensin A, 4-bromo-* phenyl urethane | 1 | 2 | 21 | — | —* | 225 | 178 |
| Monensin A, phenyl-* urethane | 10 | 2 | 26 | — | —* | 229 | 170 |
| Monensin A, 4-chloro- phenyl urethane | 1 | 5 | 20 | 5 | 19 | 224 | 179 |
| Monensin A, 4-fluoro- phenyl urethane | 3 | 2 | 17 | — | —* | 220 | 182 |
| Monensin A, 4-methyl- phenyl urethane | 1 | 3 | 16 | 4 | 15 | 217 | 182 |

*Compounds which effect blood pressure, but not heart rate are preferable
[b]The naturally occurring urethane of monensins B and A respectively. The remaining 5 urethanes are all semi-synthetized from monensin A.

The compounds of the present invention can be prepared by treating monensin A or B, viz. a compound of the general formula

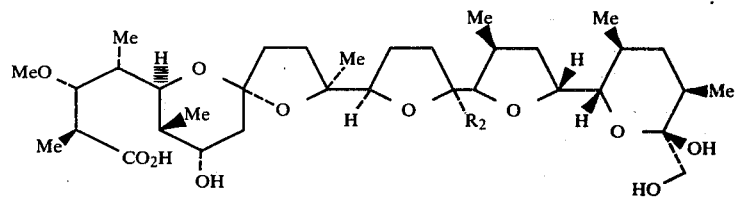

wherein $R_2$ is methyl(monensin B) or ethyl(monensin A) or a salt thereof with an isocyanate of the formula $$R_4-NCO \qquad III$$

wherein $R_4$ is as above

Preferably a salt of the starting compound of formula II is used, in particular the sodium salt. The isocyanate of formula II is preferably added in slight excess, e.g., about 10% excess so as to optimize the formation of mono derivative. The reaction is preferably carried out in an inert solvent such as a chlorinated hydrocarbon, e.g., carbon tetrachloride, methylene chloride or chloroform, ether, ethyl acetate or in an aromatic hydrocarbon solvent such as benzene or toluene. The reaction temperature is not critical but can be between above 0° C. and the boiling point of the reaction mixture, preferable at about room temperature.

EXAMPLE 1
Shake flask fermentation of Streptomyces X-14667

The X-14667 culture is grown and maintained on an Amidex agar slant having the following composition (grams/liter distilled water):

| Amidex | 10.0 |
|---|---|
| N-Z amine A | 2.0 |
| Beef extract | 1.0 |
| Yeast extract | 1.0 |
| CoCl$_2$ . 6H$_2$O | 0.02 |
| Agar | 20.0 |

The slant is inoculated with X-14667 culture and incubated at 28° C. for 7-14 days. A chunk of agar containing the sporulated culture from the agar slant is then used to inoculate a 500-ml Erlenmeyer flask containing 100 ml sterilized inoculum medium having the following composition (grams/liter distilled water):

| Tomato pomace | 5.0 |
|---|---|
| Distillers soluble | 5.0 |
| OM peptone | 5.0 |
| Debittered yeast | 5.0 |
| Corn starch | 20.0 |
| CaCO$_3$ | 1.0 |
| K$_2$HPO$_4$ | 1.0 |

Adjust pH to 7.0 with NaOH before sterilization.

The inoculated inoculum medium is incubated at 28° C. for 48-72 hours on a rotary shaker, operating at 250 rpm with a 2-inch stroke.

A 3 ml portion (3%, v/v) of the resulting culture is then used to inoculate a 500-ml Erlenmeyer flask containing 100 ml sterilized production medium having the following composition (grams/liter distilled water):

| Tomato pomace | 5.0 |
|---|---|
| Distillers soluble | 5.0 |
| OM peptone | 5.0 |
| Debittered yeast | 5.0 |
| Corn starch | 20.0 |
| CaCO$_3$ | 1.0 |
| K$_2$HPO$_4$ | 1.0 | pH is adjusted to 7.0 with NaOH before autoclaving.

The inoculated medium is incubated at 28° C. for 5 days on a rotary shaker running at 250 rpm with a 2-inch stroke.

EXAMPLE 2

Tank fermentation of Streptomyces X-14667

The X-14667 culture is grown and maintained on a starch casein agar slant having the following composition (grams/liter distilled water):

| | |
|---|---|
| Soluble starch | 10.0 |
| Casein | 1.0 |
| $K_2HPO_4$ | 0.5 |
| $MgSO_4$ (anhydrous) | 0.5 |
| Agar | 20.0 |

Adjust to pH 7.4 with NaOH before autoclaving.

The slant is inoculated with X-14667 culture and incubated at 28° C. for 7–10 days. A chunk of agar from the sporulated culture is then used to prepare vegetative inoculum by inoculating a 500-ml Erlenmeyer flask containing 100 mls of inoculum medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 | pH is adjusted to 7.0 before autoclaving.

The inoculated medium is incubated for 96 hours at 28° C. on a rotary shaker operating at 250 rpm, 2-inch stroke.

Twenty ml (1%, v/v) of this culture are used to inoculate a 6-liter Erlenmeyer flask containing 2 liters of medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 | pH is adjusted to 7.0 before autoclaving at 15–20 pound pressure for 45 minutes.

The inoculated medium is incubated for 72 hours at 28° C. on a rotary shaker operating at 250 rpm.

Six liters of this culture are used to inoculate 60 gallons of the following medium in a 100 gallon fermentor (grams/liter tap water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |
| Sag 4130 Antifoam (Union Carbide) | 0.1 |

The pH of the medium is adjusted to 7.0 with NaOH before sterilization for 1¼ hours with 60 lb/in² steam.

The inoculated medium is aerated with compressed air at a rate of 3 cubic feet per minute and is stirred with agitators at 280 rpm. The fermentation is carried out at 28° C. for 5 days.

EXAMPLE 3

Isolation of Monensin A, Monensin B and diphenethylurea

The whole broth from a 60 gallon fermentation of Streptomyces sp. X-14667 was extracted at pH 7.6 with an equal volume of ethyl acetate. The solvent layer was separated and concentrated under reduced pressure to 1.0 liter. The solvent concentrate was washed sequentially with equal volumes of 1 N HCl, water, saturated sodium carbonate, and water and then was dried over sodium sulfate. Further concentration and filtration gave a crystalline mixture, containing Monensin A, Monensin B and diphenethylurea and an oil.

EXAMPLE 4

Isolation of Monensin A and diphenethylurea

The 5.4 grams of mixed crystals were dissolved in 100 ml of methylene chloride and washed with 1 N HCl. The solvent layer was concentrated to a small volume and on addition of n-hexane, diphenethylurea, (mp 136° C.) was separated by filtration.

The filtrate (mother liquor) was diluted with diethylether, washed with saturated sodium carbonate and upon concentration and addition of hexane crystalline monensin B, (mp 276° C.) was separated and a second crop of crystals was also recovered.

By repeated thin layer chromatography on silica gel (development solvent, ethylacetate) it was determined that the second crop of crystals was a mixture of monensin B and monensin A.

EXAMPLE 5

Isolation of Monensin A, 2-phenethylurethane and Monensin B, 2-phenethylurethane The 39.4 grams of oil from the first filtration was dissolved in hexane (0.47 liters) and extracted twice with 0.47 liters of acetonitrile. The extracts were pooled, concentrated to an oil, and washed with n-hexane. The n-hexane insoluble, oily solid was dissolved in diethyl ether, filtered, and chromatographed on 500 grams of silica gel eluting with a gradient between 5 liters methylene chloride to 5 liters of methylene chloride-ethanol (9:1). Fractions of ~18 ml each were collected and #120 to 180 were pooled for rechromatography. Fractions #185 to 235 were pooled, concentrated under reduced pressure to an oily solid, dissolved in diethyl ether and washed successively with 1 N HCl, saturated sodium carbonate, and water. The solvent was concentrated under reduced pressure to give monensin B, 2-phenethylurethane sodium salt as a powder, mp 70° C. $[\alpha]_D +48°$ ($CHCl_3$, C=1%), +44° ($CH_3OH$, C=1%). Calc.: $C_{44}H_{68}NO_{12}Na$ (826.98): C, 63.90; H, 8.41; N, 1.69; Na, 2.78. Found: C, 64.45; H, 8.68; N, 1.76; Na, 2.31.

Two hundred mg of the sodium salt was dissolved in ethylacetate and washed with 1 N HCl. The solvent was concentrated under reduced pressure yielding 100 mg of a beige powder, mp 50° C. $[\alpha] +59.6°$ ($CHCl_3$, C=1%); +45.8° ($CH_3OH$, C=1%). Calc.: $C_{44}H_{69}NO_{12}$ (804.4): C, 65.65; H, 8.76; N, 1.74; O, 23.85. Found: C, 65.53; H, 8.16; N, 1.49; O, 24.16.

The pooled fractions #120 to 180 were concentrated under reduced pressure to an oil and rechromatographed on a 700 g. silica gel column. The column was eluted initially with 4 liters of ethyl acetate, then 4 liters of ethyl acetate-acetone (1:1), and finally 4 liters of ethyl acetate ethanol (95:1). The ~18 ml fractions, #29 to 35 (pooled) upon concentration yielded diphenethylurea. The pooled fractions #86 to 121 upon concentration yielded 2 grams of Monensin B, 2-phenethylurethane. The pooled fractions, #55 to 85 were concentrated under reduced pressure to an oily solid, and rechromatographed on the Waters Prep-500 two column unit using hexane-acetone (8:2). The two component mixture was resolved to give Monensin B, 2-phenethylurethane and Monensin A, 2-phenethylurethane, the latter as a powder upon concentration, mp 103° C. $[\alpha]_D$ 50° (CHCl$_3$, C=1%) Calc.: C$_{45}$H$_{70}$NO$_{12}$Na (840.04); C, 64.34; H, 8.40; N, 1.67; Na, 2.73. Found: C, 64.43; H, 8.29; N, 1.92; Na, 2.49.

These structures of the end products were confirmed by synthesis from Monensin A and B respectively. The semi-synthetic material was prepared in both cases by dissolving 1 mmole of the antibiotic in benzene and adding 1.2 mmole of 2-phenethyl iso cyanate. After reacting overnight, the compounds were worked up by washing the reaction mixture with aqueous Na$_2$CO$_3$ and evaporating the solvent under reduced pressure. The crude reaction products were purified by silica gel chromatography as described for the end products. The semi-synthetic and natural products were shown to be identical by mp., $[\alpha]_D$, UV spectrum, IR, NMR and MS.

EXAMPLE 6

Preparation of the 4-bromophenylurethane of monensin A from monensin A, free acid Ten millimoles (6.89 g) of monensin A hydrate was dissolved in benzene (100 ml.) and to this solution, and excess (11 mmole) of 4-bromophenyl isocyanate in an equal volume of benzene, was added and the reaction stirred at room temperature. The course of the reaction was followed by silica gel TLC using ethyl acetate-hexane-ethanol (80:20:2) as development solvent and vanillin-phosphoric acid reagent for detection.

After one week, the reaction appeared complete and the reaction mixture was washed in turn with 0.5 N HCl, water, saturated Na$_2$CO$_3$ and water. The benzene solution was dried (Na$_2$SO$_4$) and evaporated under reduced pressure to an amorphous solid. The derivative was crystallized from acetonitrile to yield 4-bromophenylaminocarbonyloxy-(0-11)-monensin, sodium salt, mp 201° to 203° C., $[\alpha]_D$+65.3° (CHCl$_3$, C=1%). Calcd. for C$_{43}$H$_{66}$O$_{12}$NBrNa (891.87), %C, 57.90; H, 7.46; N, 1.57; Br, 8.96. Found: %C, 58.57; H, 7.36; N, 1.23; Br, 8.90.

EXAMPLE 7

Preparation of 4-bromophenylurethane of monensin A from the sodium salt of monensin Starting with 5 g. of the monensin, sodium salt (7 mmole) and 2 g. of 4-bromophenyl isocyanate, the reaction was run as in Example 6, but the sodium salt appeared to react faster and by TLC, the reaction was complete after two days.

After work-up as before, there was produced 4-bromophenylaminocarbonyloxy-(0-11)-monensin.

EXAMPLE 8

Following the teachings of Examples 6 and 7, there may be produced by utilizing the appropriate commercially available isocyanate the following compounds:

| Compound | MP | $[\alpha]$D |
|---|---|---|
| Monensin A, n-methylurethane | 191–193° C. | |
| Monensin A, 4-bromophenethylurethane | 201–203° C. | |
| Monensin B, (R)-1-phenethylurethane | 89–93° C. | |
| Monensin A, phenylurethane | 199–210° C. | |
| Monensin A, 4-chlorophenylurethane | 199–207° C. | |
| Monensin B, (S)-1-phenethylurethane | 116–120° C. | |
| Monensin A, cyclohexylurethane | 110–123° C. | |
| Monensin A, 2-(phenyl)-cyclopropyl urethane | 119–124° C. | |
| Monensin A, 4-fluorophenylurethane | 199–223° C. | |
| Monensin A, 4-nitrophenylurethane | 189–192° C. | +104.7° (1%, CH$_3$CN) |
| Monensin A, 4-methyl phenylurethane | 220° C. | +59.6° (1%, CHCl$_3$) |
| Monensin A, 4-iodophenylurethane | 203–206° C. | +67.6° (1%, CHCl$_3$) |
| Monensin A, N-butylurethane | | +59.2° (1%, CHCl$_3$) |
| Monensin A, 4-phenoxyphenylurethane | 210–213° C. | +67.9° (1%, CHCl$_3$) |

EXAMPLE 9

Preparation of (phenyl ethyl isocyanate)

40 grams of phenethyl amine in 300 ml of dry toluene saturated with dry HCl gas was mixed until a heavy white precipitate formed. An additional 200 ml of dry toluene was added with 50 ml of phosgene (12.5% in benzene). The mixture was refluxed (10 min.) and then 450 ml of phosgene was slowly added over 30 minutes and the mixture refluxed for 4 hours. The reaction mixture was allowed to cool to room temperature slowly and the solvent removed in vacuo leaving a yellow oil. Vacuum distillation of the oil at 82° to 83° C./0.1 mm yield 1.8 g of end product.

EXAMPLE 10

| | TABLET FORMULATIONS: (Wet Granulation) | | |
|---|---|---|---|
| Item | Ingredients | mg/tablet | mg/tablet | mg/tablet |
| 1. | Monensin B, 2-phenethylurethane or Monensin A, 2-phenethylurethane | 15 | 30 | 60 |
| 2. | Lactose | 188 | 173 | 188 |
| 3. | Modified Starch | 25 | 25 | 30 |
| 4. | Pregelatinized Starch | 20 | 20 | 20 |
| 5. | Distilled water q.s. | — | — | — |
| 6. | Magnesium stearate | 2 | 2 | 2 |
| | Weight of tablet | 250 mg | 250 mg | 300 mg |

PROCEDURE (1) Mix Items 1-4 in a suitable mixer.
(2) Granulate with sufficient distilled water to proper consistency. Mill
(3) Dry in a suitable oven.
(4) Mill and mix with magnesium stearate.
(5) Compress on a suitable press for 3 minutes equipped with appropriate punches.

EXAMPLE 11

TABLET FORMULATIONS: (Direct Compression)

| Item | Ingredients | mg/tablet | mg/tablet | mg/tablet |
|---|---|---|---|---|
| 1. | Monensin B, 2-phenethylurethane or Monensin A, 2-phenethylurethane | 15 | 30 | 60 |
| 2. | Lactose | 207 | 192 | 162 |
| 3. | Avicel | 45 | 45 | 45 |
| 4. | Direct Compression Starch | 30 | 30 | 30 |
| 5. | Magnesium Stearate | 3 | 3 | 3 |
|  | Weight of tablet | 300 mg | 300 mg | 300 mg |

PROCEDURE (1) Mix Item 1 with equal amount of lactose. Mix well.
(2) Mix with Item 3, 4, and remaining amount of Item 2. Mix well.
(3) Add magnesium stearate and mix for 3 minutes.
(4) Compress on a suitable punch.

EXAMPLE 12

CAPSULE FORMULATIONS:

| Item | Ingredients | mg/capsule | mg/capsule | mg/capsule |
|---|---|---|---|---|
| 1. | Monensin B, 2-phenethylurethane or Monensin A, 2-phenethylurethane | 15 | 30 | 60 |
| 2. | Lactose | 239 | 224 | 194 |
| 3. | Starch | 30 | 30 | 30 |
| 4. | Talc | 15 | 15 | 15 |
| 5. | Magnesium Stearate | 1 | 1 | 1 |
|  | Capsule fill weight | 300 mg | 300 mg | 300 mg |

PROCEDURE (1) Mix items 1-3 in a suitable mixer.
(2) Add talc and magnesium stearate and mix for a short period of time.
(3) Encapsulate on an appropriate encapsulation machine.

What is claimed:

1. A compound of the formula wherein $R_1$ is hydrogen, wherein $R_4$ is alkyl, phenyl, pyridyl, furyl, 4-alkylphenyl, 4-halophenyl, 4-nitrophenyl, 4-phenoxyphenyl, 4-alkoxyphenyl, 4-alkylcarbonylphenyl, 4-phenylcarbonylphenyl, phenyl, furyl or pyridyl substituted lower alkyl, 4-halophenylalkyl, 2-phenylcycloalkyl, acetyl, propionyl or butyryl substituted phenyl, pyridyl or furyl cycloalkyl; $R_2$ is methyl or ethyl and $R_3$ is —$CONHR_4$ and their pharmaceutically acceptable salts.

2. The compound of claim 1 wherein $R_2$ is ethyl.

3. The compound: Monensin B, 2-phenethylurethane and the pharmaceutically acceptable salts thereof.

4. The compound: Monensin A, 2-phenethylurethane and the pharmaceutically acceptable salts thereof.

5. A process to produce a compound of the formula wherein $R_1$ is hydrogen, wherein $R_4$ is alkyl, phenyl, pyridyl, furyl, 4-alkylphenyl, 4-halophenyl, 4-nitrophenyl, 4-phenoxyphenyl, 4-alkoxyphenyl, 4-alkylcarbonylphenyl, 4-phenylcarbonylphenyl, phenyl, furyl or pyridyl substituted lower alkyl, 4-halophenylalkyl, 2-phenylcycloalkyl, acetyl, propionyl or butyryl substituted phenyl, pyridyl or furyl and cycloalkyl; $R_2$ is methyl or ethyl and $R_3$ is —$CONHR_4$ which comprises reacting a compound of the formula wherein $R_2$ is as above with an isocyanate of the formula $R_4$-NCO wherein $R_4$ is as above in an inert solvent.

* * * * *